United States Patent [19]

Levesque et al.

[11] Patent Number: 4,594,150
[45] Date of Patent: Jun. 10, 1986

[54] MONO- AND DITHIOIC ESTERS, THEIR PREPARATION AND USES

[75] Inventors: Guy Levesque, Caen; Pierre Tozzolino, Morlaas, both of France

[73] Assignee: Societe Nationale Elf Aquitaine (Production), France

[21] Appl. No.: 618,464

[22] Filed: Jun. 8, 1984

[30] Foreign Application Priority Data

Jun. 10, 1983 [FR] France ............... 83 09639

[51] Int. Cl.$^4$ ............................................. B03D 1/02
[52] U.S. Cl. ..................................... 209/166; 252/61
[58] Field of Search ............... 209/166, 167; 252/61; 260/455 R

[56] References Cited

U.S. PATENT DOCUMENTS 4,274,950 6/1981 Larribau et al. .
4,455,262 6/1984 Detienne et al. .

FOREIGN PATENT DOCUMENTS 2396545 8/1981 France .
1282493 7/1972 United Kingdom ............ 260/455 R Primary Examiner—Bernard Nozick
Attorney, Agent, or Firm—Ostrolenk, Faber, Gerb & Soffen

[57] ABSTRACT

Mono- and dithioic esters, the alcohol residue of which carries a group including one or more oxygen atoms, are prepared by the action of an oxygen-containing organic compound, carrying an active atom, upon a mixed magnesium salt of a mono- or dithioic acid,

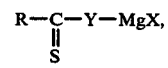

where Y is O or S, R is a hydrocarbon group and X is a halogen. The product obtained is treated with an aqueous acid. The new products so synthesized are of the type

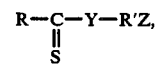

notably those where R' is a chain, —(CH$_2$)$_n$—, with n=1 to 12, Z being —OH or —COOH and are used as a collector in the flotation of minerals.

7 Claims, No Drawings

MONO- AND DITHIOIC ESTERS, THEIR PREPARATION AND USES

The present invention relates to a new class of thiocarboxylic compounds; it relates more particularly to mono- and dithioic esters where the alcohol residue carries at least one functional group containing oxygen. The invention also comprises a process for the preparation of these compounds, as well as applications of the latter. An important application is the use of such products as collectors in the flotation of minerals.

Various thiocarboxylic derivatives are known and used in industry, for example in cosmetics or in the enrichment of minerals. This is the case, for example, with dithio-acids and their esters, described in French Patent Publications Nos. 2396545, 2504131, 242617 and 2458319. However, industry is not concerned with compounds which, adjacent their mono- or dithioic function, carry other functional groups. However, research on which the present invention is based has clearly shown that these kinds of compounds have an increased utility; in fact, modification of the solubility or affinity for various substances, particularly for certain cations—which results from the presence of a second function in the thio- or dithio-acid molecule—leads to compounds of improved activity. This is the case for example with use of the substances in question as constituents of cosmetic compositions, as flotation agents for minerals, complexing agents for metals etc.

The new products according to the invention are thio-esters or dithio-esters where the alcohol residue includes at least one functional group containing oxygen, more particularly at least one free or combined hydroxyl or carboxyl group. The additional group or groups can be located in any possible position with respect to the atom of O or S to which the alcohol residue is connected in the thio or dithio-ester. The remotest position often has considerable advantages.

The compounds according to the invention can be represented by the diagrammatic general formula:

     (1)

in which
R is an alkyl or alkenyl group, particularly $C_1$–$C_{24}$ and most particularly $C_1$–$C_8$, which can carry an aryl substituent; an aryl group, particularly phenyl, where one or more of the H atoms can be substituted by alkyl groups or halogens; or an alkoxy group, preferably from $C_2$ to $C_{18}$.
Y is S or O;
R' is an aliphatic linear or branched chain, —$(CH_2)_n$—, n preferably being 1 to 12 and more particularly 1 to 6, any branches preferably comprising —$C_mH_{2m+1}$ with m=1 to 4;
Z represents an —OH, —OR", —COOH, —COOR", —$CONH_2$, —CONHR" or —CON(R")$_2$ function, where R" is a $C_1$ to $C_8$ alkyl or alkenyl group or a phenyl group which can be alkylated, it being understood that Z is not necessarily at the end of the R' chain, but can constitute a side branch of it.

In the compounds which are particularly interesting from the practical standpoint, R is a methyl, ethyl or propyl group or also a phenyl group, Y is S, R" is from $C_1$ to $C_6$, while Z, being —OH or —COOH, is located at an $\alpha$, $\beta$, $\gamma$, or $\omega$ position with respect to Y.

Thus, typical examples of the new products according to the invention are hydroxy and carboxy-methyl, -ethyl, -propyl, -isopropyl, -butyl, -isobutyl, -tert. butyl, -pentyl, -hexyl, etc. dithioates (ethane-dithioates), propane-dithioates, butane-dithioates, benzene-dithioates and toluene-dithioates.

The invention also comprises a process of preparation of the compounds described above, which allows the latter to be obtained in good yields in a desirable state of purity. This process utilizes a Grignard reaction, known per se, but has not previously been employed on substances used according to the invention nor in the conditions involved in it.

The process according to the invention uses a mixed magnesium salt of a mono- or dithioic acid,

     (2)

or

     (2')

where R has the same meaning as in formula (1) given above, X being a halogen; this salt is reacted with an oxygen-containing organic compound containing an active atom, capable of being attached to the magnesium compound, after which the product obtained is treated with an acid to eliminate the magnesium and its anion.

Compounds with an active atom particularly utilizable according to the invention are aldehydes, epoxides and salts of halogenated organic acids.

Thus, for the first time according to the invention, a magnesium atom in a thioic group is reacted with an aldehyde, epoxide or halo acid, to synthesize an ester or a mono- or dithioic acid.

With an aldehyde, the first stage of the process can be represented by the equation:

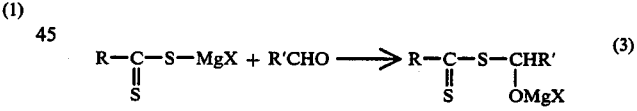     (3)

In the case of an epoxide, the reaction can be written as:

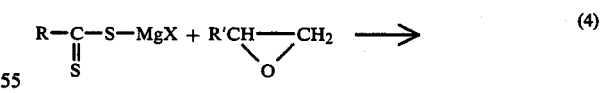     (4)

When the reactant employed is an organic halo acid salt of the type X—$(CH_2)_n$COOM, where X is a halogen, n is an integer, generally from 1 to 18, and M is a cation, preferably alkalimetal, the reaction scheme is as follows:

     (5)

-continued $$R-\underset{\underset{S}{\|}}{C}-S-(CH_2)_n COOM + MgX_2$$

The second stage of treating the magnesium complex obtained with an acid, such as HCl, H$_2$SO$_4$, HClO$_4$ etc, causes elimination of the —MgX of the product formed by the reactions (3) or (4) or the cation M according to (5). This gives:
according to reaction (3):

$$R-\underset{\underset{S}{\|}}{C}-S-\underset{\underset{OH}{|}}{CHR'}$$

according to reaction (4):

$$R-\underset{\underset{S}{\|}}{C}-S-\underset{\underset{OH}{|}}{CH_2CHR'}$$

according to reaction (5):

$$R-\underset{\underset{S}{\|}}{C}-S-(CH_2)_n COOH$$

which constitutes the desired compounds according to the invention.

The preparation of a mixed magnesium starting salt of formula (2) or (2') by reacting carbon disulphides, CS$_2$, with a magnesium salt, RMgX, in a solvent, has been known for a long time (J. HOUBEN & L. KESSELKAUL, Chem. Ber. 35, 1902, p. 3695) and is not therefore described in detail here.

In contrast, the first stage according to the invention, where the purpose is the reaction of an oxygen-containing organic compound, carrying an active atom, upon this mixed magnesium salt (2) or (2'), while analogous to the reactions of halo alkyl groups with magnesium salts (J. M. BEINER & A. THUILLIER, C. R. Acad. Sc, Paris t. 274-7.2.1972), has novel particularities not encompassed by the known art. It is known in fact that the reaction with halo alkyl groups becomes more difficult as the molecular weight of the alkyl group increases; it is then necessary to operate at temperatures of about 50° C., which affects the purity of the product obtained (J. MEIJER et coll., Recueil de Travaux Chim. des Pays-Bas, 92, 1973, p. 602-4). Contrary to this known art, in the process of the invention, the reactions (3) to (5), which take place in an anhydrous solvent, are carried out in general at temperatures not exceeding 20° C. and preferably between 0° and 10° C. Thus, operation does not proceed at the low temperatures of the order of −10° to −15° C. recommended by certain authors, nor approaching 50° C., but in a specific range from 0° to 20° or preferably from 0° to 10° C., which allows industrially a sufficient speed of reaction, while ensuring suitable purity.

The solvent in which the reactions (3) to (5) take place can be selected from various liquids which are nonreactive vis-à-vis the magnesium compounds; tetrahydrofuran is particularly recommendable. It also has the advantage of being suitable for the preparation of the initial magnesium salt (2) or (2') using a magnesium compound, RMgX, and CS$_2$, as the reaction according to the invention can be effected in the same medium in which preparation of the magnesium salt (2) or (2') has taken place.

The invention is illustrated non-limitatively by the Examples which follow.

EXAMPLES 5 TO 5

First, 3 liters of solution in tetrahydrofuran are prepared from 6 moles of the mixed magnesium salt of dithio-acetic acid, $$CH_3-\underset{\underset{S}{\|}}{C}-S-MgCl,$$

in known manner; for this, 6 moles of CH$_3$Cl are reacted with 6 gram atoms of Mg in 3000 ml of tetrahydrofuran, after which 6 moles of CS$_2$ are added, the mixture being maintained at 5° C. for 1 hour.

According to the new characteristic of the invention, to an aliquot fraction of 500 ml of the solution obtained, 1 mole of reactant, which varies from one example to the other and is explained in the Table below, is added. The mixture so formed is maintained at 5° C. for 5 hours, to allow the reaction (3) or (4) indicated above to take place.

Then the medium is acidified with 200 ml of cooled 7N HCl and extraction of the organic compounds present is effected by means of methylene chloride; the extract is washed with dilute cold HCl and then neutralized with sodium bicarbonate. After a final washing with water, the organic extract is dried over anhydrous Na$_2$SO$_4$. After the solvents have evaporated, the remaining product is distilled under reduced pressure.

The reactants utilized and the characteristics of the compounds obtained are as follows.

| Ex. | Reactant | Compound obtained | Boiling point/ mm/Hg: |
|---|---|---|---|
| 1 | Formaldehyde | Hydroxymethyl-dithioacetate (Yield 85%) CH$_3$CS$_2$CH$_2$OH | 54°–56°/13 mm |
| 2 | Acetaldehyde | 1-Hydroxyethyl dithioacetate (Yield 90%) CH$_3$CS$_2$CH—CH$_3$ $\mid$ OH | 31°–33°/1 mm |
| 3 | Ethyleneoxide | 2-Hydroxyethyl-dithioacetate (Yield 80%) CH$_3$CS$_2$CH$_2$CH$_2$OH | 78°–80°/13 mm |
| 4 | Epoxy-1, 2-butane | 2-Hydroxybutyl-dithioacetate (Yield 73%) CH$_3$CS$_2$CH$_2$CH—C$_2$H$_5$ $\mid$ OH | 74°–76°/13 mm |
| 5 | Epoxy-1, 2-isobutane | 2-Hydroxy-2-methyl-propyl-dithioacetate (Yield 92%) CH$_3$CS$_2$CH$_2$—C(CH$_3$)$_2$ $\mid$ OH | 75°–77°/13 mm |

EXAMPLE 6

Preparation of the magnesium salt is analogous to that of the foregoing Examples, but the methyl chloride, $CH_3Cl$, is replaced by phenyl chloride, $C_6H_5Cl$, which produces a solution of the mixed magnesium salt in benzene-dithioic acid,

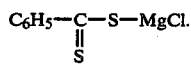

This is treated with formaldehyde in the gaseous state at the ratio of 1 mole per 1 mole of magnesium compound. The product obtained in a yield of 72% is hydroxymethyl-benzene-dithioate, $C_6H_5—CS_2—CH_2OH$, boiling at 82°–86° C. under 0.1 mm Hg.

Examples 1 to 6, compared with those in Table II, page 644 of Comptes Rendus de l'Acad. Sc. Paris, t.274, 7.2.1972 indicated above, show a considerable improvement in yields, viz. 72% to 92% as against 37% to 71%, in relation to the fixation of alkyl or phenyl groups not carrying a functional group.

EXAMPLES 7 TO 11

Reaction of mixed magnesium salts of dithioic acids with sodium chloroacetate

In each example, another compound,

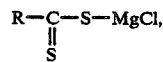

is used, prepared from a different RCl, according to the operative mode of Examples 1 to 5.

To each of the solutions obtained, 1 mole of $ClCH_2COONa$ in a 43% concentrated solution in water is added, per mole of magnesium dithioate. After 24 hours at 20° C., the resultant solution is concentrated by evaporation under reduced pressure and then acidified with 200 ml of 12N HCl. The organic phase is decanted. By chromatographic purification over silica, the carboxymethyl dithio-esters below are obtained.

| Example No | R of initial magnesium salt | Yield % | Ester obtained | Melting point |
|---|---|---|---|---|
| 7 | $CH_3\!\!\diagdown\!\!\!\!\!\!\!\phantom{x}\\ \phantom{xxx}CHCH_2CH_2—\\ CH_3\!\!\diagup\!\!\!\!\!\!\!\phantom{x}$ | 63 | $CH_3\!\!\diagdown\!\!\!\!\!\!\!\phantom{x}\\ \phantom{xxx}CHCH_2CH_2CS_2CH_2COOH\\ CH_3\!\!\diagup\!\!\!\!\!\!\!\phantom{x}$ | 35° C. |
| 8 | $CH_3—$ | 47 | $CH_3CS_2CH_2COOH$ | 77° C. |
| 9 | $CH_3CH_2CH_2CH_2—$ | 66 | $CH_3(CH_2)_3CS_2CH_2COOH$ | 13° C. |
| 10 | $CH_3(CH_2)_6—$ | 61 | $CH_3(CH_2)_6CS_2CH_2COOH$ | 49–50° C. |
| 11 | $C_6H_5—$ | 65 | $C_6H_5—CS_2CH_2COOH$ | 122° C. |

APPLICATIONS

Examples 12 to 22 which follow illustrate the application of the invention to various particular minerals. The operative mode employed in these Examples comprises the treatment of a pulp constituted by 1 g of mineral of particles of 63 to 160 microns in 300 ml of water, this pulp being placed in a Hallimond cell.

Under magnetic agitation, sulphuric acid or caustic soda is added in order to adjust the pH of the pulp to the desired value. After the addition to the pulp of an appropriate quantity of the thioic compound, in solution in ethyl alcohol or tetrahydrofuran, a current of nitrogen of about 10 l/h is passed into the base of the cell through a sintered filter No. 3. The flotation operation itself is effected for 3 minutes. The particles of the mineral entrained to the surface are recovered, dried and weighed; the percentage of the flotated quantity of the mineral recovered is thus determined with respect to the pulp treated.

Tests have been effected with 0.1 ml of a 1/1000 alcoholic or THF solution of the collector, which corresponds to 100 g of collector per tonne of mineral.

For comparison, Examples 20–22 use K amyl xanthate, known as one of the best of the collectors employed industrially at the present.

All the tests have been effected at ambient temperature.

The following table gives the results of these tests.

EXAMPLES 12 to 22

| | | | % flotated: | | | |
|---|---|---|---|---|---|---|
| Ex No | Compound | pH | galena | blende | chalco-pyrite | pyrites |
| 12- | $CH_3(CH_2)_3\underset{\underset{S}{\|\|}}{C}SCH_2OH$ | | | | | |
| | Hydroxymethyl-dithiopentanoate | 5.5 | 93 | 92.5 | 78 | 77 |
| 13- | " | 7.05 | 90 | 90 | 70.5 | 70 |
| 14- | " | 9.02 | 96 | 15 | 87 | 80.5 |
| 15- | " | 10.50 | 93 | 16 | 84 | 86 |
| 16- | $CH_3\!\!-\!\!\underset{\underset{CH_3}{\|}}{C}HCH_2CH_2\underset{\underset{S}{\|\|}}{C}SCH_2OH$ | | | | | |
| | Hydroxymethyl-dithio-4-methyl pentanoate | 5.55 | 92 | 95 | 68 | 52 |
| 17- | " | 7.07 | 92 | 93.5 | 66 | 31 |

-continued

EXAMPLES 12 to 22

| Ex No | Compound | pH | % flotated: galena | blende | chalco-pyrite | pyrites |
|---|---|---|---|---|---|---|
| 18- | " | 9.01 | 94 | 39 | 80 | 51 |
| 19- | " | 10.50 | 92 | 17 | 79 | 76 |
|  | Potassium-amyl-xanthate | 5.5 | 90 |  |  |  |
| 20- | " | 7.05 | 86 |  |  |  |
| 21- | " | 9.00 | 85 |  |  |  |
| 22- | " | 10.50 | 79 |  |  |  |

The results obtained fully prove the utility of the compounds according to the invention in the flotation of minerals. In the case of galena, the best yields are obtained with esters where the dithioic acid is from $C_5$ to $C_8$ (Examples 12 to 19) and, quite remarkably, operation can advantageously be carried out at any pH from 5 to 11. These esters are superior to the excellent collector of the known art, potassium-amyl-xanthate, the efficacy of which reduces at a pH of 7 (Examples 20 to 22).

For blende, the same esters of dithioic acids are particularly suitable at pH values not exceeding 7; towards pH 10, the amount of mineral flotated becomes low (particularly Examples 14, 15 and 19), which can become of advantage for separation from galena and/or chalcopyrite.

We claim:

1. A method of carrying out the flotation of copper, iron, lead or zinc sulfide minerals from an ore, wherein an aqueous pulp of said minerals is added with 10 to 500 grams of a collector per ton of the ore, the collector being constituted by a compound of the formula

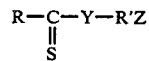

where R is an alkyl of 1 to 6 carbon atoms, phenyl or toluyl, Y is S, R' is a straight or branched alkylene group of 1 to 6 carbon atoms, Z is —OH and is located at any position of the alkylene, and then air is bubbled through the pulp and the froth and said sulfide minerals thus formed is recovered.

2. Method according to claim 1, wherein R is phenyl.

3. Method according to claim 2, wherein the collector is hydroxymethyl benzene dithioate.

4. Method according to claim 1, wherein R is alkyl.

5. Method according to claim 4, wherein the collector is hydroxyethyl dithioacetate, 2-hydroxyethyl dithioacetate, 2-hydroxybutyl dithioacetate or 2-hydroxy-2-methylpropyl dithioacetate.

6. Method according to claim 4, wherein R is methyl.

7. Method according to claim 4 wherein the collector is hydroxy-methyl dithiopentanoate or hydroxy-methyl dithio-4-pentanoate.

* * * * *